Sept. 29, 1936. A. FREY Plant Pat. 196
FREESIA
Filed March 16, 1936
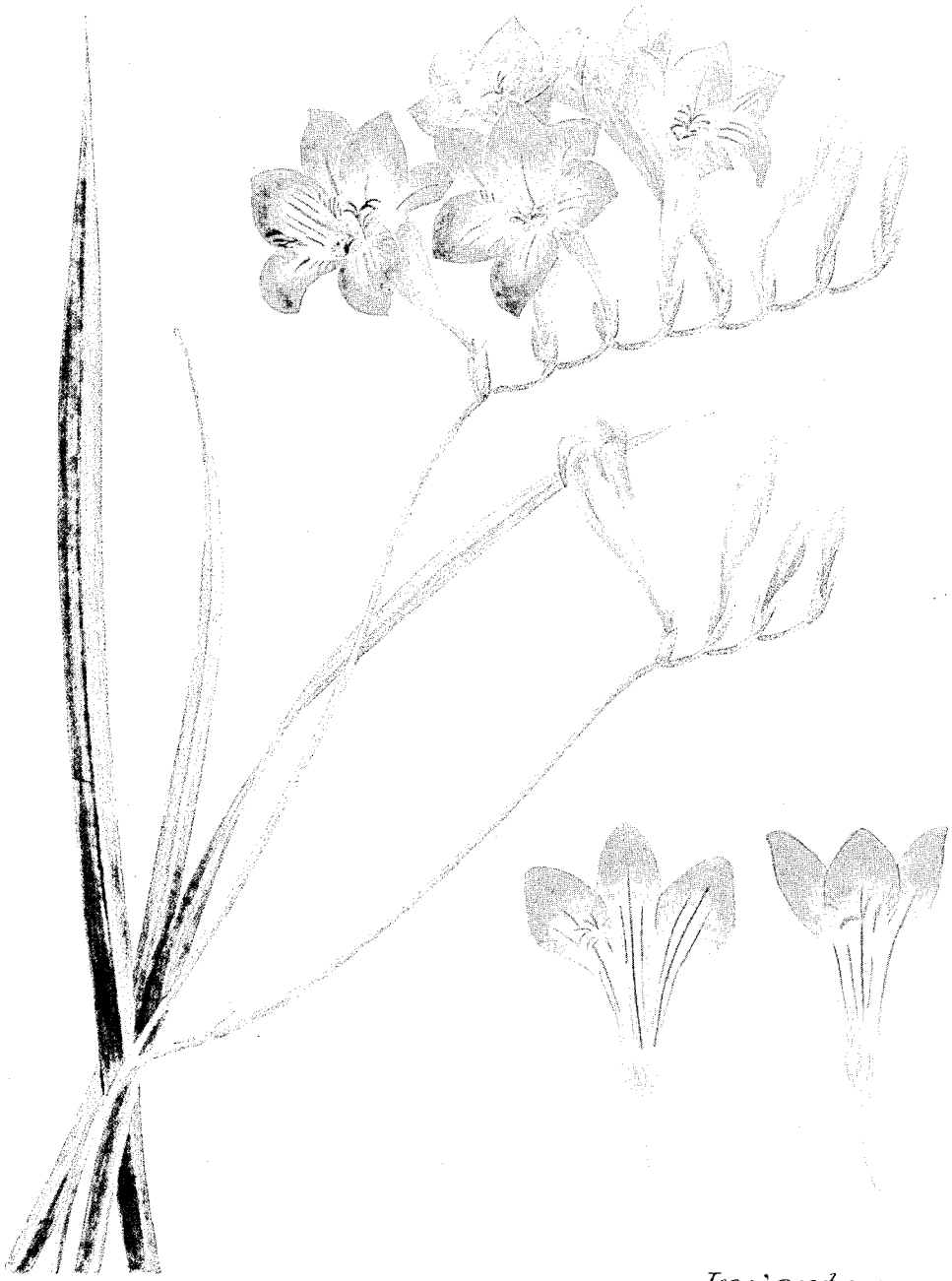
Inventor
Alois Frey
by Rummler Rummler & Woodworth
Attys Patented Sept. 29, 1936

Plant Pat. 196

UNITED STATES PATENT OFFICE

196

FREESIA

Alois Frey, San Fernando, Calif.

Application March 16, 1936, Serial No. 69,111

1 Claim. (Cl. 47—60)

This invention relates to freesias of the tinted or colored type.

The object of this invention in general is to provide a more desirable coloring in the class known as "red freesias", a larger number of blossoms of a deeper shade, stiff stems, with usually three or four long lateral spikes providing for as many successive cuttings, and other desirable and useful characteristics that will be hereinafter revealed.

To attain these objects repeated careful selections and crossings were made of various unnamed but numbered freesias of the type mentioned, until the results sought for were accomplished, and became known as #0.443.

The newness and distinctiveness of this new freesia were recognized by the Commercial Flower Growers of Chicago from observations made at Vaughan's greenhouses at Western Springs, Illinois, where these freesias were also grown and displayed, and a certificate of merit was awarded at their regular meeting in February, 1936.

The accompanying illustration shows in approximately natural size and colors a branch of this new freesia with five fully opened flowers, several buds, and a lateral from the same general branch in a less mature stage. To further identify this new freesia, a typical blossom is split in two showing the inside of both halves, depicting the coloration and difference in markings in each set of lobes.

The following is a detailed description of this new variety of freesia, all references to color being based on Maerz & Paul's "Dictionary of Color", edition of 1930.

The plant is very upright in growth; an easy, vigorous grower; free flowering; clean foliage; and will produce under average greenhouse conditions spikes 33 inches long. There are commonly 3 or 4 "piquant green" (Plate 20-K-6) sturdy laterals from 7 to 9 inches long from each bulb.

Usually 8 blossoms are found on a single spike, although this may vary. They are borne upright along a rachis that is only slightly irregular and which is smoothly and gracefully bent at right-angles to the vertical stem or peduncle.

The blossoms when fully open measure 1¼ to 1¾ inches across the top and average 2 inches in height. The perianth is tubular, long and gracefully slender. The six segments or lobes at the top of the perianth are broad and overlapping, slightly pointed, turning back very widely when fully opened to display all inside coloring, but are not bent abruptly at a right angle to the tube or perianth as is usual with some varieties.

Four or five blossoms on a spike are commonly open at one time with one or more buds beginning to show color.

Three "amethyst" (Plate 45-J-8) anthers show prominently in the throat of the blossom, as well as the six-branched pale yellow pistil. The ovary is ovoid, three-celled.

This variety of freesia has a sweet, pleasing odor.

Color: The general tonality of fully opened blossoms is "blood red" (Plate 3-L-11) or "afghan red" (Plate 5-L-6), the upper area of the petal lips being "afghan red", and the middle portion "blood red". The throat is lighter, being "cadmium yellow" (Plate 9-L-8) becoming "light chrome" (Plate 10-L-4) at the base of the tube, both inside and outside.

In newly opened blossoms, the upper area of the petal lips is "blood red" and the middle area "poinsettia" (Plate 2-L-9) which changes to the darker tones described above as the blossoms develop. On the inside of the petals one major and several fine median "blood red" stripes extend from the upper area of the petal lips down to the lower area of the tubes, while a number of short horizontal lines of "poinsettia" are to be found extending inwardly from the edge of the petal lips in the middle area on alternate lips. These stripes and markings are not visible on the outside of the tube.

On the outside upper area of most lobes, the color is "Tyrian violet" (Plate 44-K-5).

The first color that appears in the buds is "orchadee" (Plate 42-H-4) changing to "imperial purple" (Plate 45-L-10) and "Tyrian violet" as the "blood red" of the blossoms begin to show.

The sepals are 2 in number, "piquant green" (Plate 20-K-6) and loose fitting.

On the stems close to the point of attachment of each blossom, there is a touch of "olive drab" (Plate 15-J-5).

The most important characteristics which in combination, I believe, distinguish my new variety from all other freesias are:

First: Distinctive "afghan" or "blood" red color with "cadmium yellow" throat.

Second: Large number of blossoms produced on each spike with four or five commonly displayed at the same time.

Third: Its upright, vigorous growth with stiff stems and laterals.

Fourth: Its producing three to four long laterals from each bulb, assuring as many successive cuttings.

Fifth: Its ease of growth, clean foliage and free flowering qualities.

I claim:

A new and distinct variety of freesia as shown herein and described, characterized particularly by its distinctive afghan or blood red color with cadmium yellow throat, free flowering habit, easy and vigorous growth, stiff stems, and having 3 to 4 long laterals, assuring as many successive cuttings.

ALOIS FREY.